United States Patent
Kawasaki et al.

(10) Patent No.: US 9,555,026 B2
(45) Date of Patent: Jan. 31, 2017

(54) SOLID DISPERSION COMPRISING AMORPHOUS CILOSTAZOL

(71) Applicant: OTSUKA PHARMACEUTICAL CO., LTD., Tokyo (JP)

(72) Inventors: Junichi Kawasaki, Osaka (JP); Atsuya Nakamura, Osaka (JP); Naoki Kamada, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/764,663

(22) PCT Filed: Feb. 5, 2014

(86) PCT No.: PCT/JP2014/053232
§ 371 (c)(1),
(2) Date: Jul. 30, 2015

(87) PCT Pub. No.: WO2014/123244
PCT Pub. Date: Aug. 14, 2014

(65) Prior Publication Data
US 2015/0366859 A1      Dec. 24, 2015

(30) Foreign Application Priority Data

Feb. 6, 2013   (JP) ................. 2013-021475

(51) Int. Cl.
*A61K 9/14*       (2006.01)
*A61K 31/4709*    (2006.01)
*A61K 9/20*       (2006.01)
*A61K 9/24*       (2006.01)

(52) U.S. Cl.
CPC .......... *A61K 31/4709* (2013.01); *A61K 9/146* (2013.01); *A61K 9/209* (2013.01); *A61K 9/2031* (2013.01); *A61K 9/2054* (2013.01)

(58) Field of Classification Search
CPC ...... A61K 9/146; A61K 9/2031; A61K 9/209; A61K 9/2054; A61K 31/4709
See application file for complete search history.

(56) References Cited

U.S. PATENT DOCUMENTS

| | | |
|---|---|---|
| 5,762,944 A | 6/1998 | Inoue et al. |
| 6,254,889 B1 | 7/2001 | Kigoshi et al. |
| 6,350,786 B1 | 2/2002 | Albano et al. |

(Continued)

FOREIGN PATENT DOCUMENTS

| | | |
|---|---|---|
| JP | 5649378 A | 5/1981 |
| JP | 11-246404 A | 9/1999 |

(Continued)

OTHER PUBLICATIONS

International Search Report for PCT/JP2014/053232 dated Apr. 14, 2014.

(Continued)

*Primary Examiner* — Blessing M Fubara
(74) *Attorney, Agent, or Firm* — Sughrue Mion, PLLC

(57) ABSTRACT

The present invention relates to a solid dispersion comprising cilostazol, and methacrylic acid copolymer S and/or methacrylic acid copolymer L, which is characterized in that cilostazol is retained in an amorphous state in a gastrointestinal tract for a certain period after oral administration.

10 Claims, 5 Drawing Sheets

(56) References Cited

U.S. PATENT DOCUMENTS

| | | | |
|---|---|---|---|
| 2004/0185102 A1* | 9/2004 | Friesen | A61K 9/146 424/486 |
| 2009/0047357 A1 | 2/2009 | Tomohira et al. | |
| 2010/0172989 A1* | 7/2010 | Roth | A61K 9/2027 424/484 |
| 2011/0165236 A1 | 7/2011 | Chow et al. | |

FOREIGN PATENT DOCUMENTS

| | | |
|---|---|---|
| JP | 2000-095708 A | 4/2000 |
| JP | 2001-163769 A | 6/2001 |
| JP | 2008-521878 A | 6/2008 |
| JP | 2010-526848 A | 8/2010 |
| JP | 2011-500511 A | 1/2011 |
| JP | 2011-520774 A | 7/2011 |
| KR | 10-2013-0013157 A | 2/2013 |
| WO | 93/07217 A1 | 4/1993 |
| WO | 96/21448 A1 | 7/1996 |
| WO | 97/04782 A1 | 2/1997 |
| WO | 00/57881 A1 | 10/2000 |
| WO | 2006/059224 A1 | 6/2006 |
| WO | 2007/072908 A1 | 6/2007 |
| WO | 2008/138755 A2 | 11/2008 |
| WO | 2009/051022 A2 | 4/2009 |
| WO | WO 2009/051022 A2 * | 4/2009 |
| WO | 2009/139504 A2 | 11/2009 |
| WO | 2010/026971 A1 | 3/2010 |

OTHER PUBLICATIONS

International Preliminary Report on Patentability for PCT/JP2014/053232 dated Aug. 20, 2015.

* cited by examiner

SOLID DISPERSION COMPRISING AMORPHOUS CILOSTAZOL

CROSS REFERENCE TO RELATED APPLICATIONS

This application is a National Stage of International Application No. PCT/JP2014/053232 filed Feb. 5, 2014, claiming priority based on Japanese Patent Application No. 2013-021475 filed Feb. 6, 2013, the contents of all of which are incorporated herein by reference in their entirety.

TECHNICAL FIELD

The present invention relates to a solid dispersion comprising amorphous cilostazol. In detail, the present invention relates a solid dispersion comprising cilostazol, and methacrylic acid copolymer S and/or methacrylic acid copolymer L; and a pharmaceutical composition comprising the solid dispersion.

In addition, the present invention also relates to processes preparing the solid dispersion, and the pharmaceutical composition comprising the solid dispersion.

BACKGROUND ART

Cilostazol is 6-[4-(1-cyclohexyl-1H-tetrazol-5-yl)butoxy]-3,4-dihydrocarbostyril as shown in the following formula (1), which exhibits high inhibitory action for platelet aggregation as well as inhibitory action for phosphodiesterase, antiulcer activity, hypotensive action, antiphlogistic action, etc. (Patent Reference 1) and thereby is widely used in clinical use as a drug for treating various ischemic symptoms caused by chronic arterial occlusion such as ulcer, pain and coldness. And, cilostazol has been additionally approved as a medicament having an indication which prevents the relapse after treatment of cerebral infarction (except cardiogenic cerebral infarction).

The cilostazol tablets which are called Pletaal® OD tablets 50', Pletaal® OD tablets 100', and Pletaal® powder 20% (OTSUKA PHARMACEUTICAL CO., LTD.) have already been on sale.

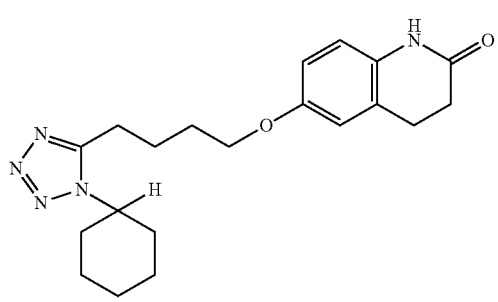

(1)

Usually, cilostazol is orally administered twice a day for an adult, but it has been desired to develop a new sustained-release formulation of cilostazol which can be absorbed in an intestinal track slowly but for a long time even by one administration, because the main subject of the drug is an elderly patient and it has been necessary to reduce the development of side effects such as headache. In addition, it has been also desired that a new formulation of cilostazol which is little affected by a food because cilostazol is susceptible to a food, for example, the $C_{max}$ and AUC of cilostazol administered after meal are 2.3 and 1.4 times higher than those of fasting, respectively.

For the purpose of developing such a sustained-release formulation, there have been a variety of studies to improve the release control and absorption of the poorly-soluble drug, cilostazol in lower gastrointestinal tract (Patent References 2 to 5).

In order to improve the dissolution and absorption of a poorly-soluble drug, in general, various means such as a micronization (nano-particulation), a solubilization with surfactants and oil, and also a solid dispersion method are used.

The solid dispersion method is carried out by dispersing a drug in an inert excipient, in many instances, a drug exists in an amorphous state in the solid dispersion. Thus, the solid dispersion method is often used as an initial method to make an amorphous drug. As a process of preparing a solid dispersion, some methods are known, for example, coprecipitating method, spray drying method, hot-melt method, and hot-melt extrusion method. For a skilled person, the most-used method among them is spray drying method, but the other methods are seldom used.

Patent Reference 6 discloses that a poorly-soluble compound is dispersed in a water-insoluble ionic polymer such as Eudragit® so that a powder of a poorly-soluble compound can be stabilized as an amorphous material. And, Patent Reference 7 discloses a process of preparing a solid dispersion comprising an amorphous compound by coprecipitating or hot-melt extruding a very insoluble imidazolidine derivative referred to as HEP with hypromellose acetate succinate (HPMC-AS).

In general, a compound in an amorphous state is unstable toward water. In particular, a high crystallinity compound in an amorphous state is unstable, which is known to be easily crystallized by the absorption of moisture or by being suspended with water. Thus, it is a big challenge to inhibit the crystallization of a formulation containing such an amorphous compound in a body, in case that the formulation is, for example, a sustained release formulation which stays in a gastrointestinal tract for long time after oral administration.

Cilostazol has an extremely low solubility in water, and has a high crystallinity, thereby it was very difficult to prepare a solid dispersion comprising a stable amorphous cilostazol. Even though a solid dispersion comprising an amorphous cilostazol can be successfully prepared through some effort of process or formula, cilostazol will easily crystallize when suspended in water. Thus, it was very difficult to apply an amorphous cilostazol to a sustained release formulation which contacts to water for a long time.

PRIOR ART

Patent Reference

[Patent Reference 1] JP 56(1981)-49378 A
[Patent Reference 2] JP 2011-520774 A
[Patent Reference 3] JP 2001-163769 A
[Patent Reference 4] WO 2007/072908
[Patent Reference 5] JP 2011-500511 A
[Patent Reference 6] JP 2000-095708 A
[Patent Reference 7] JP 2010-526848 A

SUMMARY OF INVENTION

Problems to be Solved by the Invention

The purpose of the present invention is to provide a solid dispersion comprising cilostazol, characterized in that cilostazol having an extremely low solubility in water and a high crystallinity is retained in an amorphous state in a gastrointestinal tract for a certain period after oral administration.

Means to Solve the Problems

The present inventors have intensively studied and found that it is possible to prepare a solid dispersion (extrudate) comprising cilostazol which can be retained in a stable amorphous state in an aqueous suspension, by hot-melting or hot-melt extruding a mixture of cilostazol and methacrylic acid copolymer S and/or methacrylic acid copolymer L which is an enteric polymer in a certain ratio. Based upon the new findings, the present invention has been completed.

The present invention provides pharmaceutical compositions and use thereof as shown in the following [1] to [10].

[1] A solid dispersion comprising (i) cilostazol and (ii) methacrylic acid copolymer S and/or methacrylic acid copolymer L, wherein cilostazol is dispersed in an amorphous state in the methacrylic acid copolymer.

[2] The solid dispersion of [1] which is prepared by hot-melt or hot-melt extrusion.

[3] The solid dispersion of [2] which is prepared by hot-melt extrusion.

[4] The solid dispersion of any one of [1] to [3] wherein the ratio of (i) cilostazol and (ii) methacrylic acid copolymer S and/or methacrylic acid copolymer L is 1:0.5 to 1:3 by weight.

[5] The solid dispersion of any one of [1] to [3] wherein the ratio of (i) cilostazol and (ii) methacrylic acid copolymer S and/or methacrylic acid copolymer L is 1:1 to 1:3 by weight.

[6] The solid dispersion of any one of [1] to [5] wherein (ii) methacrylic acid copolymer S and/or methacrylic acid copolymer L is methacrylic acid copolymer S.

[7] The solid dispersion of any one of [1] to [5] wherein (ii) methacrylic acid copolymer S and/or methacrylic acid copolymer L is methacrylic acid copolymer L.

[8] A pharmaceutical composition comprising the solid dispersion of any one of [1] to [7].

[9] An oral formulation comprising the pharmaceutical composition of [8].

[10] A process of preparing a solid dispersion which comprises hot-melting or hot-melt extruding (i) cilostazol and (ii) methacrylic acid copolymer S and/or methacrylic acid copolymer L, and then cooling and milling the extruded product.

Effect of the Invention

Cilostazol in the present solid dispersion can be stably retained in an amorphous state, and even when the solid dispersion is suspended in water, all or most of the contained cilostazol can be retained in an amorphous state at least for 24 hours. Thereby, it is expected that cilostazol in the present solid dispersion can be retained in an amorphous state in a gastrointestinal tract for a long time after oral administration.

In addition, the present solid dispersion has a very strong acid-resistance since it comprises methacrylic acid copolymer S and/or methacrylic acid copolymer L which is an enteric polymer. This property enables the solid dispersion not to be dissolved in the stomach, but to be dissolved in lower section of the small intestine where is in a high pH range simultaneously to elute out cilostazol via the behavior that methacrylic acid copolymer S and/or methacrylic acid copolymer L are rapidly dissolved there. As a result, the present solid dispersion is expected to make cilostazol dissolved in lower section of a gastrointestinal tract and improve the absorption of cilostazol.

DESCRIPTION OF EMBODIMENTS

Figure 1:
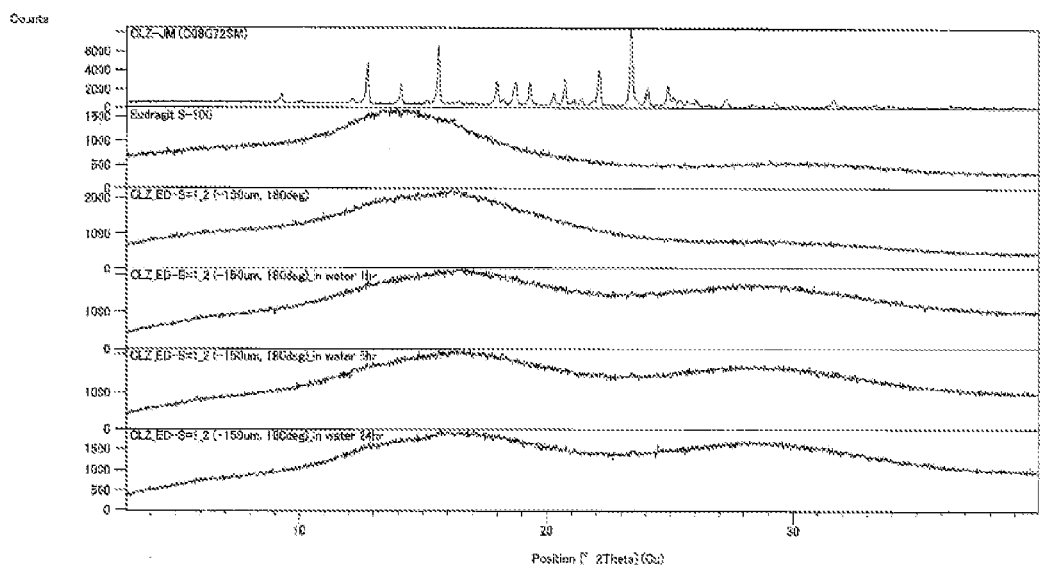
FIG. 1 represents an analytical result in powder X-ray diffraction that the stability in an aqueous suspension of the solid dispersion prepared by hot-melt extrusion of cilostazol and methacrylic acid copolymer S (Eudragit® S 100) was evaluated. The top pattern of the powder X-ray diffraction shows a result in powder X-ray diffraction with a jet-milled crystalline cilostazol, the second top pattern of the powder X-ray diffraction shows a result in powder X-ray diffraction with methacrylic acid copolymer S (Eudragit® S 100), the third top pattern of the powder X-ray diffraction shows a result in powder X-ray diffraction with the solid dispersion (<150 μm) prepared in Example 3 in which the ratio of cilostazol and methacrylic acid copolymer S is 1:2, the fourth top pattern of the powder X-ray diffraction shows a result in powder X-ray diffraction with the solid dispersion (<150 μm) of Example 3 which was stored as an aqueous suspension at 37° C. for 1 hour after preparing the suspension, the fifth top pattern of the powder X-ray diffraction shows a result in powder X-ray diffraction with the solid dispersion (<150 μm) of Example 3 which was stored as an aqueous suspension at 37° C. for 5 hours after preparing the suspension, and the bottom pattern of the powder X-ray diffraction shows a result in powder X-ray diffraction with the solid dispersion (<150 μm) of Example 3 which was stored as an aqueous suspension at 37° C. for 24 hours after preparing the suspension.

Cilostazol can be prepared, for example, by the process disclosed in JP-56-49378 A.

As methacrylic acid copolymer S and methacrylic acid copolymer L used herein, for example, Eudragit® S 100 and Eudragit® L 100 provided by EVONIK Industries are well known respectively, both of which have an anionic copolymer structure composed of methacrylic acid and methyl methacrylate. Methacrylic acid copolymer S is composed of the acid and the ester in a ratio of about 1:2, and methacrylic acid copolymer L is composed of the acid and the ester in a ratio of about 1:1. The average molecular weight of the both is about 123,000. Methacrylic acid copolymer S has a property to be dissolved at pH range of 7 or higher, and methacrylic acid copolymer L has a property to be dissolved at pH range of 6 or higher. Through the properties of the pH dependency, the both are known as an enteric coating agent.

The term "methacrylic acid copolymer S and/or methacrylic acid copolymer L" in the present invention mean that the both can be contained or either of them can be contained. And, the both ingredients can be contained in any ratio since the both can bring in the character of the present invention.

Regarding the solid dispersion of the present invention, the weight ratio of (i) cilostazol, and (ii) methacrylic acid copolymer S and/or methacrylic acid copolymer L is not limited as long as the ratio is in about 1:0.1 to about 1:10, but generally about 1:0.5 or more, preferably about 1:1 or more, more preferably about 1:1 to about 1:5, even more preferably about 1:1 to about 1:3, and most preferably about 1:2.

The process of preparing the present solid dispersion includes hot-melt and hot-melt extrusion. In detail, these methods are characterized by uniformly mixing a drug, a polymer and optional excipients; melting the mixture by heating; and then cooling it. In these methods, a conventional method and device such as a mixer and kneader equipped with heat source can be used.

In the hot-melt or the hot-melt extrusion, an extruder equipped with a screw in the barrel (cylinder) (e.g., single screw extruder, twin screw extruder, etc.) can be used. Among these extruders, a twin screw extruder has recently become mainstream.

An extruder is composed of five main parts, i.e., hopper (input structure), motor (controlling the rotation of screw), screw (primary source for shearing a material and moving it), barrel (housing a screw and controlling the temperature), and die (outlet) (controlling the shape and size of extrudate).

Therein, a drug, a polymer, and optional excipients are thrown into the machine via the hopper, in which the temperature of the hot-melt is suitably retained, and then the solid mixture is melted by the rotation of the screw to be kneaded uniformly. Or, it is possible to preliminarily mix the ingredients before throwing them into the machine, as appropriate.

The polymer used in the hot-melt extrusion is not limited as long as it is a natural or artificial polymer compound to be generally used as a material for pharmaceutical formulation and additionally the function of the polymer does not disappear when discharged from the die in a twin screw extruder, which includes a pH dependent polymer, a pH independent polymer, and a water-soluble polymer. In the present invention, methacrylic acid copolymer S and/or methacrylic acid copolymer L are used as such polymer.

In the hot-melt extrusion, other excipients besides the above-mentioned polymer may be also used herein. Such excipients are not limited as long as they are what are generally used as a material for pharmaceutical formulation and additionally they do not damage the function of the present solid dispersion.

The setting condition in the process of the present invention such as pressure, temperature, speed of supplying material powder, diameter of die, shape of screw, and rotary speed of screw depends on the types of the used drug, polymer and extruder. It is important to combine each suitable condition to keep the process temperature under the decomposition temperatures of the drug and the polymer, and it is necessary to vary each condition in response to the character of the desired product.

In the hot-melt method or the hot-melt extrusion method, generally it is necessary to heat to make the process temperature over the glass-transition temperature of the drug and the polymer. On the other hand, from the viewpoint of the stability of the drug, polymer and excipients for decomposition or denaturation, the heat temperature needs to be set suitably, in general 200° C. or lower, preferably about 180° C. or lower is chosen.

The very preferred polymer in the present invention includes methacrylic acid copolymer S (Eudragit® S 100) and methacrylic acid copolymer L (Eudragit® L 100), whose glass-transition temperatures are very high, about 160° C. and about 150° C., respectively. In order to hot-melt extrude these polymers, it is necessary to heat them over their glass-transition temperatures, but such high temperatures can cause the decomposition of the polymers themselves. The inventors actually studied the preparation of hot-melt extrusion products using methacrylic acid copolymer S and methacrylic acid copolymer L, but it was very difficult to extrude the methacrylic acid copolymer S or methacrylic acid copolymer L alone. Thus, it was confirmed that methacrylic acid copolymer S and methacrylic acid copolymer L are not suitable for the extruding by hot-melt at all. Thus, many prior references suggest the possibility to use methacrylic acid copolymer S and methacrylic acid copolymer L in hot-melt extrusion (hot-melt and extrusion), but there have not been any actually successful examples of such preparation in the past.

The melting point of cilostazol contained in the present solid dispersion is 160° C. to 180° C. In order to make a high crystallinity cilostazol in an amorphous state, it is necessary to make cilostazol melted completely.

The present inventors have found that it is possible to stably prepare a solid dispersion comprising amorphous cilostazol by hot-melt extruding cilostazol together with methacrylic acid copolymer S and/or methacrylic acid copolymer L which are difficult to be extruded alone, without decomposing the polymers. And also, the present inventors have found that all or most of cilostazol in the prepared solid dispersion can be retained in an amorphous state at least for 24 hours even when the solid dispersion is suspended in water.

The solid dispersion of the present invention is preferably prepared as follows:

Preliminarily, cilostazol and methacrylic acid copolymer S (Eudragit® S 100) and/or methacrylic acid copolymer L (Eudragit® L 100) are mixed.

The mixed powder is supplied into a twin screw extruder in a constant supply speed of 10 to 200 g/min, and then it is treated in the machine at a screw speed of 50 to 300 rpm, and at a temperature of 50° C. to 300° C.

When the solid dispersion prepared herein is milled with an appropriate pulverizer, it is possible to easily prepare a particle of the solid dispersion having any desired particle size. The particle can be directly used as a powder, fine granule, or granule preparation; or further the solid dispersion of the present invention (or a particle of the solid dispersion) can be also processed, optionally adding an ingredient for pharmaceutical preparation (excipient), to a pharmaceutical composition comprising the solid dispersion. The ingredient for pharmaceutical preparation to be added here includes, for example, excipients, disintegrating agents, binders, fluidizer, lubricants, preservatives, stabilizing agent, isotonic agents, solubilizers, sweeteners, flavors, preservatives, dispersants, and pH adjusters. The excipient to be contained in the solid dispersion also includes the same.

The oral formulation of the present invention includes, for example, a solid formulation such as a tablet, a capsule, a powder, and a granule.

EXAMPLE

Hereinafter, the present invention is illustrated by the following examples, comparative examples, formulation examples and tests, but should not be construed to be limited thereto, and it is possible to vary each condition unless the variation is beyond the range of the present invention.

Preparation of Solid Dispersion by Hot-melt Extrusion

Example 1

Solid Dispersion (Methacrylic Acid Copolymer S, 0.5 Parts)

500 g of cilostazol (hammer-milled powder, Otsuka Pharmaceutical Co., Ltd.) and 250 g of methacrylic acid copolymer S (commercial name: Eudragit® S 100, Evonik Japan Co., Ltd.) were mixed in a polyethylene bag for several minutes.

The mixed powder was shaped with a twin screw extruder (KEX-25, KURIMOTO, LTD.) having dies whose gauge was 2 mmΦ, in which the barrel temperature in its kneading part was set at 100 to 180° C. and the extrusion rate was set at 100 to 150 rpm, to give a stick-shaped extrudate (solid dispersion).

The extrudate was cooled at room temperature, micronized with a pulverizer (Power Mill P-3S Model, Dalton Co., Ltd.) and another pulverizer (Fine Impact Mill 100 UPZ, Hosokawa Micron Corporation) and then screened to give a solid dispersion having a certain particle size distribution.

Example 2

Solid Dispersion (Methacrylic Acid Copolymer S, 1 Part)

500 g of cilostazol (hammer-milled powder, Otsuka Pharmaceutical Co., Ltd.) and 500 g of methacrylic acid copolymer S (commercial name: Eudragit® S 100, Evonik Japan Co., Ltd.) were mixed in a polyethylene bag for several minutes.

The mixed powder was shaped with a twin screw extruder (KEX-25, KURIMOTO, LTD.) having dies whose gauge was 2 mmΦ, in which the barrel temperature in its kneading part was set at 100 to 180° C. and the extrusion rate was set at 100 to 150 rpm, to give a stick-shaped extrudate (solid dispersion).

The extrudate was cooled at room temperature, micronized with a pulverizer (Power Mill P-3S Model, Dalton Co., Ltd.) and another pulverizer (Fine Impact Mill 100 UPZ, Hosokawa Micron Corporation) and then screened to give a solid dispersion having a certain particle size distribution.

Example 3

Solid Dispersion (Methacrylic Acid Copolymer S, 2 Parts)

500 g of cilostazol (hammer-milled powder, Otsuka Pharmaceutical Co., Ltd.) and 1000 g of methacrylic acid copolymer S (commercial name: Eudragit® S 100, Evonik Japan Co., Ltd.) were mixed in a polyethylene bag for several minutes.

The mixed powder was shaped with a twin screw extruder (KEX-25, KURIMOTO, LTD.) having dies whose gauge was 2 mmΦ, in which the barrel temperature in its kneading part was set at 100 to 180° C. and the extrusion rate was set at 100 to 150 rpm, to give a stick-shaped extrudate (solid dispersion).

The extrudate was cooled at room temperature, micronized with a pulverizer (Power Mill P-3S Model, Dalton Co., Ltd.) and another pulverizer (Fine Impact Mill 100 UPZ, Hosokawa Micron Corporation) and then screened to give a solid dispersion having a certain particle size distribution.

Example 4

Solid Dispersion (Methacrylic Acid Copolymer S, 3 Parts)

500 g of cilostazol (hammer-milled powder, Otsuka Pharmaceutical Co., Ltd.) and 1500 g of methacrylic acid copolymer S (commercial name: Eudragit® S 100, Evonik Japan Co., Ltd.) were mixed in a polyethylene bag for several minutes.

The mixed powder was shaped with a twin screw extruder (KEX-25, KURIMOTO, LTD.) having dies whose gauge was 2 mmΦ, in which the barrel temperature in its kneading part was set at 100 to 200° C. and the extrusion rate was set at 100 to 150 rpm, to give a stick-shaped extrudate (solid dispersion).

The extrudate was cooled at room temperature, micronized with a pulverizer (Power Mill P-3S Model, Dalton Co., Ltd.) and another pulverizer (Fine Impact Mill 100 UPZ, Hosokawa Micron Corporation) and then screened to give a solid dispersion having a certain particle size distribution.

Example 5

Solid Dispersion (Methacrylic Acid Copolymer L, 2 Parts 500 g of cilostazol (hammer-milled powder, Otsuka Pharmaceutical Co., Ltd.) and 1000 g of methacrylic acid copolymer L (commercial name: Eudragit® L 100, Evonik Japan Co., Ltd.) were mixed in a polyethylene bag for several minutes.

The mixed powder was shaped with a twin screw extruder (KEX-25, KURIMOTO, LTD.) having dies whose gauge was 2 mmΦ, in which the barrel temperature in its kneading part was set at 100 to 190° C. and the extrusion rate was set at 100 to 150 rpm, to give a stick-shaped extrudate (solid dispersion).

The extrudate was cooled at room temperature, micronized with a pulverizer (Power Mill P-3S Model, Dalton Co., Ltd.) and another pulverizer (Fine Impact Mill 100 UPZ, Hosokawa Micron Corporation) and then screened to give a solid dispersion having a certain particle size distribution.

Comparative Example 1

Solid Dispersion (Methacrylic Acid Copolymer S, 1 Part; Polyethylene Glycol, 0.2 Parts 500 g of cilostazol (hammer-milled powder, Otsuka Pharmaceutical Co., Ltd.), 500 g of methacrylic acid copolymer S (commercial name: Eudragit® S 100, Evonik Japan Co., Ltd.) and 100 g of polyethylene glycol (macrogol 6000, Sanyo Chemical Industries, Ltd.) were mixed in a polyethylene bag for several minutes.

The mixed powder was shaped with a twin screw extruder (KEX-25, KURIMOTO, LTD.) having dies whose gauge was 2 mmΦ, in which the barrel temperature in its kneading part was set at 100 to 170° C. and the extrusion rate was set at 100 to 150 rpm, to give a stick-shaped extrudate (solid dispersion).

The extrudate was cooled at room temperature, micronized with a pulverizer (Power Mill P-3S Model, Dalton Co., Ltd.) and another pulverizer (Fine Impact Mill 100 UPZ, Hosokawa Micron Corporation) and then screened to give a solid dispersion having a certain particle size distribution.

Comparative Example 2

Solid Dispersion (Hydroxypropyl Methylcellulose Acetate Succinate, 1 Part)

500 g of cilostazol (hammer-milled powder, Otsuka Pharmaceutical Co., Ltd.) and 500 g of hydroxypropyl methylcellulose acetate succinate (commercial name: Shin-Etsu AQOAT®, Type: AS-HF, Shin-Etsu Chemical Co., Ltd.) were mixed in a polyethylene bag for several minutes.

The mixed powder was shaped with a twin screw extruder (KEX-25, KURIMOTO, LTD.) having dies whose gauge was 2 mmΦ, in which the barrel temperature in its kneading part was set at 100 to 160° C. and the extrusion rate was set at 100 to 150 rpm, to give a stick-shaped extrudate (solid dispersion).

The extrudate was cooled at room temperature, micronized with a pulverizer (Power Mill P-3S Model, Dalton Co., Ltd.) and another pulverizer (Fine Impact Mill 100 UPZ, Hosokawa Micron Corporation) and then screened to give a solid dispersion having a certain particle size distribution.

Comparative Example 3

Solid Dispersion (Hydroxypropyl Methylcellulose Acetate Succinate, 2 Parts)

500 g of cilostazol (hammer-milled powder, Otsuka Pharmaceutical Co., Ltd.) and 1000 g of hydroxypropyl methylcellulose acetate succinate (commercial name: Shin-Etsu AQOAT®, Type: AS-HF, Shin-Etsu Chemical Co., Ltd.) were mixed in a polyethylene bag for several minutes.

The mixed powder was shaped with a twin screw extruder (KEX-25, KURIMOTO, LTD.) having dies whose gauge was 2 mmΦ, in which the barrel temperature in its kneading part was set at 100 to 150° C. and the extrusion rate was set at 100 to 150 rpm, to give a stick-shaped extrudate (solid dispersion).

The extrudate was cooled at room temperature, micronized with a pulverizer (Power Mill P-3S Model, Dalton Co., Ltd.) and another pulverizer (Fine Impact Mill 100 UPZ, Hosokawa Micron Corporation) and then screened to give a solid dispersion having a certain particle size distribution.

Preparation of Solid Dispersion by Spray Drying

Comparative Example 4

Solid Dispersion (Hypromellose Phthalate, 2 Parts)

5 g of cilostazol (hammer-milled powder, Otsuka Pharmaceutical Co., Ltd.) and 10 g of hypromellose phthalate (commercial name: HPMCP®, Grade: HP-50, Shin-Etsu Chemical Co., Ltd.) were dissolved in 300 g of a mixture of dichloromethane and ethanol (dichloromethane/ethanol=8/2 (w/w)). The solution was spray-dried with a spray dryer (GS310, Yamato Scientific Co., Ltd.) to give a solid dispersion. The spray drying was carried out under the conditions of the inlet temperature: 70° C., the spray speed: 20 g/min, and the air volume: 0.4 to 0.5 m³/min. In order to remove the residual solvent, the resulting solid dispersion was further dried with a vacuum dryer (LCV-232, TABAI ESPEC CORP.) at 50° C. for 24 hours to give a solid dispersion as a test sample.

Comparative Example 5

Solid Dispersion (Hydroxypropyl Methylcellulose Acetate Succinate, 2 Parts)

5 g of cilostazol (hammer-milled powder, Otsuka Pharmaceutical Co., Ltd.) and 10 g of hydroxypropyl methylcellulose acetate succinate (commercial name: Shin-Etsu AQOAT®, grade: AS-HF, Shin-Etsu Chemical Co., Ltd.) were dissolved in 300 g of a mixture of dichloromethane and ethanol (dichloromethane/ethanol=8/2 (w/w)). The solution was spray-dried with a spray dryer (GS310, Yamato Scientific Co., Ltd.) to give a solid dispersion. The spray drying was carried out under the conditions of the inlet temperature: 70° C., the spray speed: 20 g/min, and the air volume: 0.4 to 0.5 $m^3$/min. In order to remove the residual solvent, the resulting solid dispersion was further dried with a vacuum dryer (LCV-232, TABAI ESPEC CORP.) at 50° C. for 24 hours to give a solid dispersion as a test sample.

Comparative Example 6

Solid Dispersion (Methacrylic Acid Copolymer S, 2 Parts)

5 g of cilostazol (hammer-milled powder, Otsuka Pharmaceutical Co., Ltd.) and 10 g of methacrylic acid copolymer S (commercial name: Eudragit® S 100, Evonik Japan Co., Ltd.) were dissolved in 800 g of a mixture of dichloromethane and ethanol (dichloromethane/ethanol=8/2 (w/w)). The solution was spray-dried with a spray dryer (GS310, Yamato Scientific Co., Ltd.) to give a solid dispersion. The spray drying was carried out under the condition of the inlet temperature: 70° C., the spray speed: 20 g/min, and the air volume: 0.4 to 0.5 $m^3$/min. In order to remove the residual solvent, the resulting solid dispersion was further dried with a vacuum dryer (LCV-232, TABAI ESPEC CORP.) at 50° C. for 24 hours to give a solid dispersion as a test sample.

Comparative Example 7

Solid Dispersion (Hydroxypropylcellulose, 2 Parts)

5 g of cilostazol (hammer-milled powder, Otsuka Pharmaceutical Co., Ltd.) and 10 g of hydroxypropylcellulose (commercial name: NISSO® HPC, grade: SL, NIPPON SODA CO., LTD.) were dissolved in 300 g of a mixture of dichloromethane and ethanol (dichloromethane/ethanol=8/2 (w/w)). The solution was spray-dried with a spray dryer (GS310, Yamato Scientific Co., Ltd.) to give a solid dispersion. The spray drying was carried out under the conditions of the inlet temperature: 70° C., the spray speed: 20 g/min, and the air volume: 0.4 to 0.5 $m^3$/min. In order to remove the residual solvent, the resulting solid dispersion was further dried with a vacuum dryer (LCV-232, TABAI ESPEC CORP.) at 50° C. for 24 hours to give a solid dispersion as a test sample.

Comparative Example 8

Solid Dispersion (Hypromellose, 2 Parts)

5 g of cilostazol (hammer-milled powder, Otsuka Pharmaceutical Co., Ltd.) and 10 g of hypromellose (commercial name: TC-5®, grade: TC-5E, Shin-Etsu Chemical Co., Ltd.) were dissolved in 300 g of a mixture of dichloromethane and ethanol (dichloromethane/ethanol=8/2 (w/w)). The solution was spray-dried with a spray dryer (GS310, Yamato Scientific Co., Ltd.) to give a solid dispersion. The spray drying was carried out under the conditions of the inlet temperature: 70° C., the spray speed: 20 g/min, and the air volume: 0.4 to 0.5 $m^3$/min. In order to remove the residual solvent, the resulting solid dispersion was further dried with a vacuum dryer (LCV-232, TABAI ESPEC CORP.) at 50° C. for 24 hours to give a solid dispersion as a test sample.

Comparative Example 9

Solid Dispersion (Polyvinylpyrrolidone K25, 2 Parts)

5 g of cilostazol (hammer-milled powder, Otsuka Pharmaceutical Co., Ltd.) and 10 g of polyvinylpyrrolidone K25 (commercial name: Kollidon® 25, BASF JAPAN LTD.) were dissolved in 300 g of a mixture of dichloromethane and ethanol (dichloromethane/ethanol=8/2 (w/w)). The solution was spray-dried with a spray dryer (GS310, Yamato Scientific Co., Ltd.) to give a solid dispersion. The spray drying was carried out under the conditions of the inlet temperature: 70° C., the spray speed: 20 g/min, and the air volume: 0.4 to 0.5 $m^3$/min. In order to remove the residual solvent, the resulting solid dispersion was further dried with a vacuum dryer (LCV-232, TABAI ESPEC CORP.) at 50° C. for 24 hours to give a solid dispersion as a test sample.

Using the solid dispersion prepared by a suitable process, various pharmaceutical formulations such as a tablet, a granule and a capsule can be prepared by means of a conventional known technique. The pharmaceutical formulations can be administered via any suitable routes. In the following, some solid dispersions were suspended in water, and the change of crystalline state of cilostazol in the suspensions was evaluated with a powder X-ray diffractometer to estimate the intravital change of crystalline state of cilostazol after administering the formulation.

Test 1

With regard to each of the solid dispersions prepared in Examples 1 to 5, Comparative Examples 1 to 3, and Comparative Examples 4 to 9, the change of crystalline state of cilostazol was evaluated with a powder X-ray diffractometer, between each solid dispersion shortly after prepared and the one after suspended in water.

The measurement conditions of powder X-ray diffraction are shown below.

Measuring set: X' Pert PRO MPD (Spectris Co., Ltd.)
Optical system: parafocusing optics (transmission method)
Goniometer radius: 240 mm
Tube voltage, Tube current: 45 kV, 40 mA
Entrance slit: Soller Slit, Soller 0.04 rad
Divergence Slit ½ deg
Light-receiving slit: Soller Slit, Large Soller 0.04 rad
Antiscatter slit 5.5 mm
Measurement range: 2θ 3 to 40 deg
Scan rate: 1.11 deg/s
Sampling interval: 0.02 deg/step
Wobbled scan: Step number 5, Step size 0.02 deg Each of the micronized particles (<150 μm) prepared in the above Examples 1 to 5, and Comparative Examples 1 to 3 was measured about their powder X-ray diffraction patterns.

Separately, about 2 g of each micronized particle prepared in Examples 1 to 5, and Comparative Examples 1 to 3 which was passed with 150 μm mesh was put in a sample tube. To the sample tube was added 30 mL of purified water to prepare a suspension, and the suspension was shaken at 37° C. for 1 hour, 5 hours and 24 hours. After shaking, the suspended sample was got out of the sample tube, the excess water was removed from the suspended sample, and then the powder X-ray diffraction pattern thereof was measured to evaluate the change of the crystalline property.

The results of the measure are shown in Table 1 below.

Figure 2:
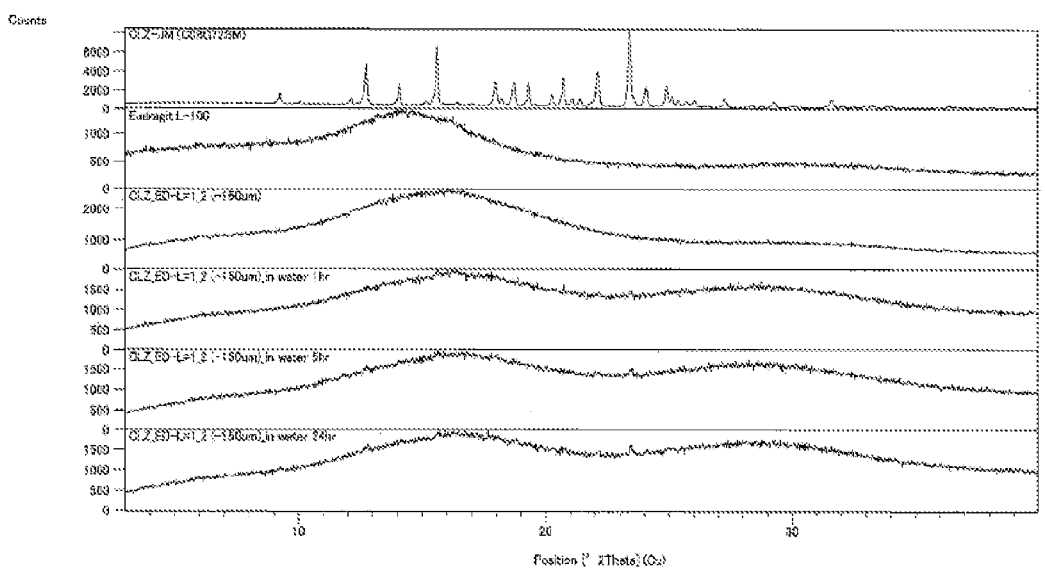
FIG. 2 represents an analytical result in powder X-ray diffraction that the stability in an aqueous suspension of the solid dispersion prepared by hot-melt extrusion of cilostazol and methacrylic acid copolymer L (Eudragit® L 100) was evaluated. The top pattern of the powder X-ray diffraction shows a result in powder X-ray diffraction with a jet-milled crystalline cilostazol, the second top pattern of the powder X-ray diffraction shows a result in powder X-ray diffraction with methacrylic acid copolymer L (Eudragit® L 100), the third top pattern of the powder X-ray diffraction shows a result in powder X-ray diffraction with the solid dispersion (<150 μm) prepared in Example 5 in which the ratio of cilostazol and methacrylic acid copolymer L is 1:2, the fourth top pattern of the powder X-ray diffraction shows a result in powder X-ray diffraction with the solid dispersion (<150 μm) of Example 5 which was stored as an aqueous suspension at 37° C. for 1 hour after preparing the suspension, the fifth top pattern of the powder X-ray diffraction shows a result in powder X-ray diffraction with the solid dispersion (<150 μm) of Example 5 which was stored as an aqueous suspension at 37° C. for 5 hours after preparing the suspension, and the bottom pattern of the powder X-ray diffraction shows a result in powder X-ray diffraction with the solid dispersion (<150 μm) of Example 5 which was stored as an aqueous suspension at 37° C. for 24 hours after preparing the suspension.
Figure 3:
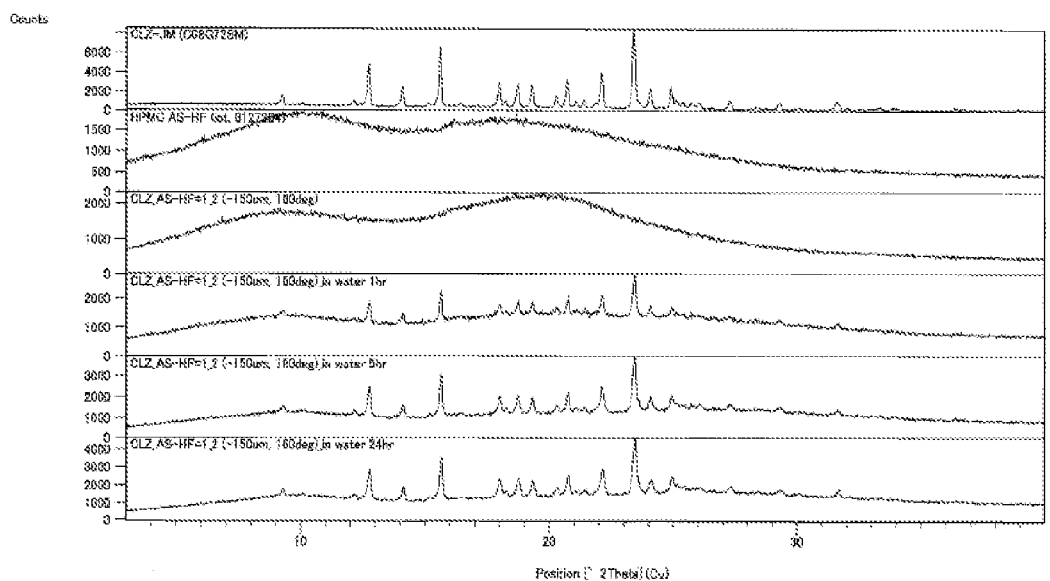
FIG. 3 represents an analytical result in powder X-ray diffraction that the stability in an aqueous suspension of the solid dispersion prepared by hot-melt extrusion of cilostazol and hydroxypropyl methylcellulose acetate succinate (Shin-Etsu AQOAT, AS-HF) was evaluated. The top pattern of the powder X-ray diffraction shows a result in powder X-ray diffraction with a jet-milled crystalline cilostazol, the second top pattern of the powder X-ray diffraction shows a result in powder X-ray diffraction with hydroxypropyl methylcellulose acetate succinate (Shin-Etsu AQOAT, AS-HF), the third top pattern of the powder X-ray diffraction shows a result in powder X-ray diffraction with the solid dispersion (<150 μm) prepared in Comparative Example 3 in which the ratio of cilostazol and hydroxypropyl methylcellulose acetate succinate (Shin-Etsu AQOAT, AS-HF) is 1:2, the fourth top pattern of the powder X-ray diffraction shows a result in powder X-ray diffraction with the solid dispersion (<150 μm) of Comparative Example 3 which was stored as an aqueous suspension at 37° C. for 1 hour after preparing the suspension, the fifth top pattern of the powder X-ray diffraction shows a result in powder X-ray diffraction with the solid dispersion (<150 μm) of Comparative Example 3 which was stored as an aqueous suspension at 37° C. for 5 hours after preparing the suspension, and the bottom pattern of the powder X-ray diffraction shows a result in powder X-ray diffraction with the solid dispersion (<150 μm) of Comparative Example 3 which was stored as an aqueous suspension at 37° C. for 24 hours after preparing the suspension.

And, the analytical results about the powder X-ray diffraction of the solid dispersion (<150 μm) prepared in Example 3, solid dispersion (<150 μm) prepared in Example 5, and the solid dispersion (<150 μm) prepared in Comparative Example 3 are shown in FIGS. 1 to 3.

In each solid dispersion shortly after prepared by the hot-melt extrusion, cilostazol existed in an amorphous state; but the solid dispersion comprising cilostazol and hydroxypropyl methylcellulose acetate succinate got quickly crystallized only in an hour after suspended in water. On the other hand, the solid dispersion comprising one or more parts by weight of methacrylic acid copolymer S or methacrylic acid copolymer L per one part by weight of cilostazol was retained in an amorphous state even 24 hours after suspended in water. In addition, when methacrylic acid copolymer S was used in the solid dispersion, but polyethylene glycol was added thereto, then the crystallization of the solid dispersion was accelerated. This result is thought to be caused by the tendency that a plasticizer or a high water-absorbing excipient such as polyethylene glycol promotes the crystallization. Thus, the solid dispersion of the present invention should not comprise such ingredient.

TABLE 1

| | Formulae | Shortly after preparation | Temperature (37° C.) | | |
|---|---|---|---|---|---|
| | | | 1 hr | 5 hr | 24 hr |
| Example 1 | cilostazol/methacrylic acid copolymer S = 1/0.5 | amorphous | crystal peak exists | crystallized | crystallized |
| Example 2 | cilostazol/methacrylic acid copolymer S = 1/1 | amorphous | still amorphous | still amorphous | still amorphous |
| Example 3 | cilostazol/methacrylic acid copolymer S = 1/2 | amorphous | still amorphous | still amorphous | still amorphous |
| Example 4 | cilostazol/methacrylic acid copolymer S = 1/3 | amorphous | still amorphous | still amorphous | still amorphous |
| Example 5 | cilostazol/methacrylic acid copolymer L = 1/2 | amorphous | still amorphous | still amorphous | still amorphous |
| Comparative Example 1 | cilostazol/methacrylic acid copolymer S/polyethyleneglycol = 1/1/0.2 | amorphous | crystal peak exists | crystal peak increases | crystallized |
| Comparative Example 2 | cilostazol/hypromellose acetate succinate = 1/1 | amorphous | crystallized | crystallized | crystallized |
| Comparative Example 3 | cilostazol/hypromellose acetate succinate = 1/2 | amorphous | crystallized | crystallized | crystallized |

Each of the spray-dried powders prepared in the above Comparative Examples 4 to 9 was measured about their powder X-ray diffraction patterns.

Separately, about 2 g of each spray-dried powder prepared in Comparative Examples 4 to 9 was put in a sample tube. To the sample tube was added about 30 mL of purified water to prepare a suspension, and the suspension was shaken at 37° C. for 1 hour. After shaking, the suspended sample was got out of the sample tube, the excess water was removed from the suspended sample, and then the powder X-ray diffraction pattern thereof was measured to evaluate the change of the crystalline property.

The results of the measure about the powder X-ray diffraction are shown in Table 2 below. The solid dispersion comprising a polymer and cilostazol which was prepared by the spray drying method was quickly crystallized shortly after suspended in water. Comparative Examples 4 and 5 were crystallized only 1 hour after suspended in water, and Comparative Example 6 was slightly crystallized. Comparative Examples 7, 8, and 9 were crystallized shortly after suspensions thereof were prepared.

TABLE 2

| | Formulae | Shortly after preparation | 37° C./1 hr |
|---|---|---|---|
| Comparative Example 4 | cilostazol/hypromellose phthalate = 1/2 | amorphous | crystallized |
| Comparative Example 5 | cilostazol/hypromellose acetate succinate = 1/2 | amorphous | crystallized |
| Comparative Example 6 | cilostazol/methacrylic acid copolymer S = 1/2 | amorphous | slightly crystallized |
| Comparative Example 7 | cilostazol/hydroxypropylcellulose = 1/2 | crystal peak exists | crystallized (shortly after suspended) |
| Comparative Example 8 | cilostazol/hypromellose = 1/2 | amorphous | crystallized (shortly after suspended) |
| Comparative Example 9 | cilostazol/polyvinylpyrrolidone K25 = 1/2 | amorphous | crystallized (shortly after suspended) |

Test 2

The dissolution property of cilostazol from the solid dispersion prepared in Example 3 which is a fine particle (<150 μm) was evaluated by the dissolution test with the following 6 test solvents.
1) 0.3% Aqueous sodium lauryl sulfate (0.30% SLS).
2) 1st Fluid (pH 1.2) for disintegration test defined in the Japanese Pharmacopoeia, containing 0.2% sodium lauryl sulfate.
3) McIlvaine buffer (pH 5.0) containing 0.2% sodium lauryl sulfate.
4) McIlvaine buffer (pH 6.8).
5) McIlvaine buffer (pH 6.8) containing 0.2% sodium lauryl sulfate.
6) McIlvaine buffer (pH 7.4).

The dissolution test was carried out according to the Japanese Pharmacopoeia, Dissolution Test, Apparatus 2 (Paddle Method). The test sample was prepared by mixing the solid dispersion containing 100 mg of cilostazol with lactose to increase the total weight 5 times that of the solid dispersion. In the test, a sinker was not used and the rotary speed of the paddle was 100 rpm. The solutions taken in every sampling time were analyzed with a spectrophotometer (UV 1200, SHIMADZU CORPORATION) to measure the concentration of cilostazol in each sampling solution.

Figure 4:
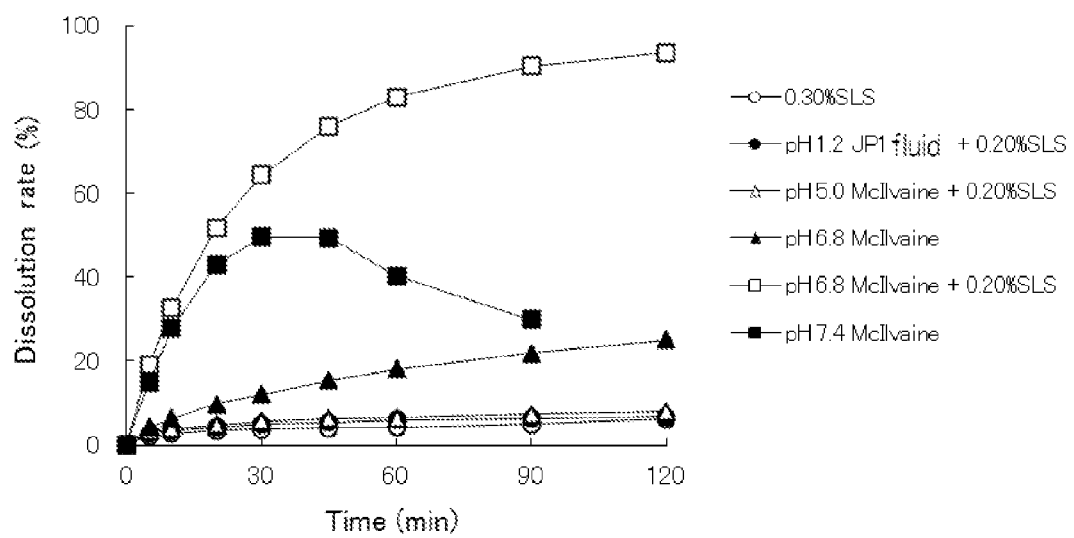
FIG. 4 represents dissolution patterns in the solid dispersion (<150 μm) of Example 3 under several pH conditions.

The result was shown in FIG. 4.

Little cilostazol was dissolved out of the test sample in water (0.3% SLS), pH 1.2 McIlvaine buffer (+0.2% SLS) or pH 5.0 McIlvaine buffer (+0.2% SLS). The result of the dissolution test using pH 6.8 McIlvaine buffer (+0.2% SLS) whose pH simulates the pH in lower gastrointestinal tract showed a fast dissolution. Accordingly, when a formulation of the present invention is administered to a human, it is expected that cilostazol can be rapidly dissolved out of the formulation to be released in its lower gastrointestinal tract.

Test 3

Using the same test method as Test 2 provided that the test solvent is pH 7.4 McIlvaine buffer, the dissolution character of cilostazol from the solid dispersion in a neutral range was evaluated.

The test samples were as follows:
1) Jet-milled powder of crystalline cilostazol (milled with a JM, Jet Mill (Spiral Jet Mill 50AS, Hosokawa Micron Corporation), the same shall apply hereinafter).
2) Micronized powder (<150 μm) of the solid dispersion prepared in Example 1.
3) Micronized powder (<150 μm) of the solid dispersion prepared in Example 2.
4) Micronized powder (<150 μm) of the solid dispersion prepared in Example 3.

Figure 5:
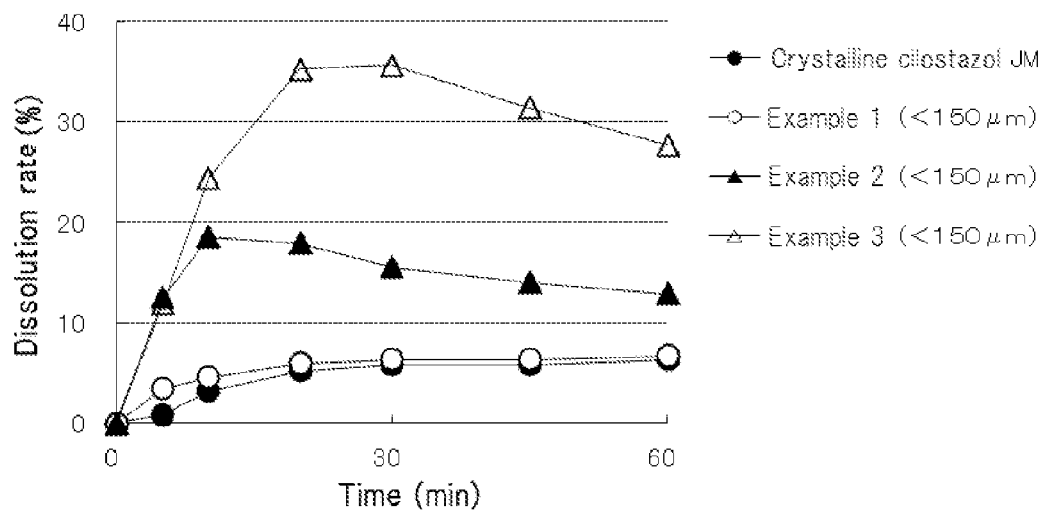
FIG. 5 represents dissolution patterns in each solid dispersion (<150 μm) of Examples 1, 2 and 3, and a jet-milled crystalline cilostazol in McIlvaine buffer (pH 7.4).

The result was shown in FIG. 5.

The dissolution of cilostazol in the solid dispersion (Example 3, <150 μm) which was prepared from the mixture of cilostazol and methacrylic acid copolymer S in a ratio of 1:2 by hot-melt extrusion was more than 5-fold faster than that of the jet-milled powder of crystalline cilostazol.

Test 4

Using the same test method as Test 2 provided that the test solvent is pH 7.4 McIlvaine buffer, the dissolution character of cilostazol from the solid dispersion in a neutral range was evaluated.

The test samples were as follows:
1) Jet-milled powder of crystalline cilostazol.
2) Micronized powder (<150 μm) of the solid dispersion prepared in Example 3.
3) Micronized powder (250 to 500 μm) of the solid dispersion prepared in Example 3.

Figure 6:
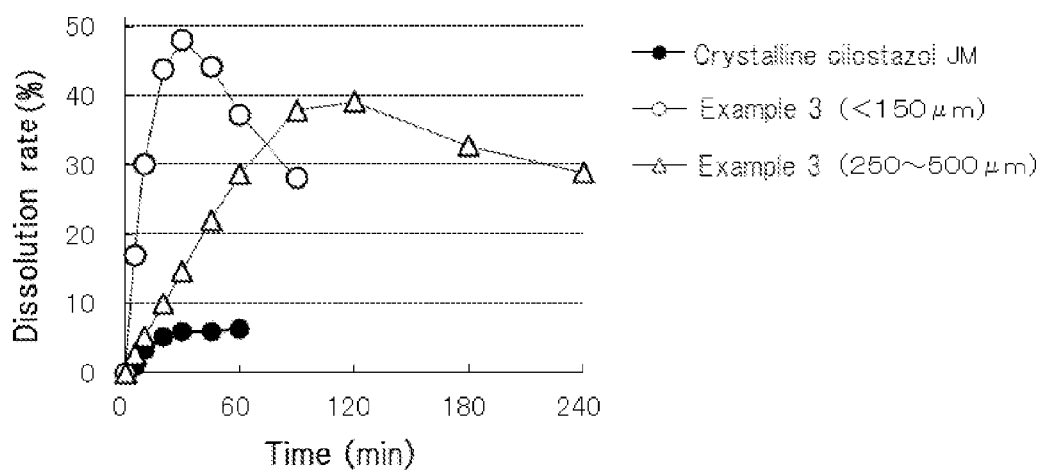
FIG. 6 represents dissolution patterns in the solid dispersions (<150 μm and 250-500 μm) of Example 3, and a jet-milled crystalline cilostazol in McIlvaine buffer (pH 7.4).

The result was shown in FIG. 6.

The result showed that the dissolution rate can be controlled by adjusting the particle size of the micronized solid dispersion.

| Formulation Example 1 | |
|---|---|
| Solid dispersion fine particle (<150 μm) of Example 3 | 300 (parts by weight) |
| Hypromellose (commercial name: METLOSE ® SR, grade: 90SH-4000SR, Shin-Etsu Chemical Co., Ltd.) | 50 (parts by weight) |
| Light anhydrous silicic acid (adsolider 101, Freund Corporation) | 3 (parts by weight) |
| Magnesium stearate (Taihei Chemical Industrial Co., Ltd.) | 1 (part by weight) |

According to the above formula, the solid dispersion fine particle, hypromellose, and light anhydrous silicic acid were mixed in a polyethylene bag, and then magnesium stearate was added thereto and further mixed. The mixed powder was compressed with a rotary tablet press machine (Clean Press, Kikusui Seisakusho Ltd.) equipped with caplet-shaped (13.6×6.8 mm) dies and punches at a tableting pressure of 1800 kg to prepare a caplet containing 100 mg of cilostazol.

| Formulation Example 2 | |
|---|---|
| Solid dispersion fine particle (<150 μm) of Example 3 | 300 (parts by weight) |
| Hydroxypropylcellulose (commercial name: NISSO ® HPC, grade: L, NIPPON SODA CO., LTD.) | 50 (parts by weight) |
| Hydroxypropylcellulose (commercial name: NISSO ® HPC, grade: M, NIPPON SODA CO., LTD.) | 50 (parts by weight) |
| Light anhydrous silicic acid (adsolider 101, Freund Corporation) | 3 (parts by weight) |
| Magnesium stearate (Taihei Chemical Industrial Co., Ltd.) | 1 (part by weight) |

According to the above formula, the solid dispersion fine particle, hydroxypropylcellulose, and light anhydrous silicic acid were mixed in a polyethylene bag, and then magnesium stearate was added thereto and further mixed. The mixed powder was compressed with a rotary tablet press machine (Clean Press, Kikusui Seisakusho Ltd.) equipped with caplet-shaped (13.6×6.8 mm) dies and punches at a tableting pressure of 1800 kg to prepare a caplet containing 100 mg of cilostazol.

| Formulation Example 3 | |
|---|---|
| Solid dispersion fine particle (<500 μm) of Example 3 | 300 (parts by weight) |
| Polyethylene oxide (commercial name: Polyox ®, grade: WSR-303, Dow Chemical) | 165 (parts by weight) |
| Light anhydrous silicic acid (adsolider 101, Freund Corporation) | 3 (parts by weight) |
| Sodium stearyl fumarate (Rettenmaier Japan Co., Ltd.) | 1 (part by weight) |

According to the above formula, the solid dispersion fine particle, polyethylene oxide, and light anhydrous silicic acid were mixed in a polyethylene bag, and then sodium stearyl fumarate was added thereto and further mixed. The mixed powder was compressed with a rotary tablet press machine (Clean Press, Kikusui Seisakusho Ltd.) equipped with caplet-shaped (13.6×6.8 mm) dies and punches at a tableting pressure of 1800 kg to prepare a caplet containing 100 mg of cilostazol.

| Formulation Example 4 | |
|---|---|
| Solid dispersion fine particle (<710 μm) of Example 3 | 300 (parts by weight) |

| Formulation Example 4 | |
|---|---|
| Polyethylene oxide (commercial name: Polyox ® grade: WSR-303, Dow Chemical) | 165 (parts by weight) |
| Light anhydrous silicic acid (adsolider 101, Freund Corporation) | 3 (parts by weight) |
| Sodium stearyl fumarate (Rettenmaier Japan Co., Ltd.) | 1 (part by weight) |

According to the above formula, the solid dispersion fine particle, polyethylene oxide, and light anhydrous silicic acid were mixed in a polyethylene bag, and then sodium stearyl fumarate was added thereto and further mixed. The mixed powder was compressed with a rotary tablet press machine (Clean Press, Kikusui Seisakusho Ltd.) equipped with caplet-shaped (13.6×6.8 mm) dies and punches at a tableting pressure of 1800 kg to prepare a caplet containing 100 mg of cilostazol.

| Formulation Example 5 | |
|---|---|
| Solid dispersion fine particle (<500 μm) of Example 3 | 300 (parts by weight) |
| Polyethylene oxide (commercial name: Polyox ®, grade: WSR-303, Dow Chemical) | 165 (parts by weight) |
| Light anhydrous silicic acid (adsolider 101, Freund Corporation) | 3 (parts by weight) |
| Magnesium stearate (Taihei Chemical Industrial Co., Ltd.) | 1 (part by weight) |

According to the above formula, the solid dispersion fine particle, polyethylene oxide, and light anhydrous silicic acid were mixed in a polyethylene bag, and then magnesium stearate was added thereto and further mixed. The mixed powder was compressed with a rotary tablet press machine (Clean Press, Kikusui Seisakusho Ltd.) equipped with caplet-shaped (13.6×6.8 mm) dies and punches at a tableting pressure of 1800 kg to prepare a caplet containing 100 mg of cilostazol.

| Formulation Example 6 | |
|---|---|
| First Layer | |
| Solid dispersion fine particle (<500 μm) of Example 3 | 225 (parts by weight) |
| Polyethylene oxide (Polyox WSR-303, Dow Chemical) | 100 (parts by weight) |
| Polyethylene glycol 6000 (Sanyo Chemical Industries, Ltd.) | 10 (parts by weight) |
| Light anhydrous silicic acid (Adsolider 101, Freund Corporation) | 3 (parts by weight) |
| Magnesium stearate (Taihei Chemical Industrial Co., Ltd.) | 1 (part by weight) |
| Second Layer | |
| Cilostazol (hammer-milled product, mean particle size: about 20 μm) | 25 (parts by weight) |
| Microcrystalline cellulose (Ceolus pH101, Asahi Kasei Chemicals Corporation) | 15.5 (parts by weight) |
| Low substituted hydroxypropyl-cellulose (commercial name: L-HPC ®, grade: LH-11, Shin-Etsu Chemical Co., Ltd.) | 5 (parts by weight) |
| Hydroxypropylcellulose (commercial name: NISSO ® HPC, grade: L, NIPPON SODA CO., LTD.) | 4 (parts by weight) wherein "2" was added as a powder, the other "2" was added as a binding solution. |
| Magnesium stearate (Taihei Chemical Industrial Co., Ltd.) | 0.5 (parts by weight) |

To prepare a powder for the first layer, the solid dispersion fine particle, polyethylene oxide, polyethylene-glycol 6000, and light anhydrous silicic acid were mixed in a drum mixer, then magnesium stearate was added thereto, and further mixed. To prepare a granule for the second layer, cilostazol, microcrystalline cellulose, low substituted hydroxypropyl-cellulose, and hydroxypropylcellulose (to be added as a powder) were put in a mixer granulator (Kneader NSK-350SR, OKADA SEIKO CO., LTD.), and the mixture was kneaded/granulated with 10% aqueous hydroxypropylcellu-lose as a binding solution, dried in FLO-COATER® (FLO-5, Freund Corporation), and size-regulated with Power Mill (P-3S type, Dalton Co., Ltd.), and then magnesium stearate was added thereto, and further mixed.

The tableting was carried out with a bi-layer tableting machine (PICCOLA BI-LAYER, RIVA) equipped with caplet-shaped (13.6×6.8 mm) dies and punches. The powder for the first layer was put on the dies and weakly compressed. Subsequently, the granule for the second layer was put around the compressed product on the same dies and compressed at a tableting pressure of about 2000 kg to prepare a bi-layer tablet containing 100 mg of cilostazol.

| Formulation Example 7 | |
|---|---|
| First Layer | |
| Solid dispersion fine particle (<500 μm) of Example 3 | 225 (parts by weight) |
| Polyethylene oxide (Polyox WSR-303, Dow Chemical) | 125 (parts by weight) |
| Hydroxypropylcellulose (commercial name: NISSO ® HPC, grade: SSL, NIPPON SODA CO., LTD.) | 20 (parts by weight) |
| Light anhydrous silicic acid (adsolider 101, Freund Corporation) | 3 (parts by weight) |
| Dibutylhydroxytoluene (Merck Ltd.) | 0.5 (parts by weight) |
| Sodium stearyl fumarate (Rettenmaier Japan Co., Ltd.) | 1.5 (parts by weight) |
| Second Layer | |
| Cilostazol (hammer-milled product, mean particle size about 20 μm) | 25 (parts by weight) |
| Microcrystalline cellulose (Ceolus pH101, Asahi Kasei Chemicals Corporation) | 15.5 (parts by weight) |
| Low substituted hydroxypropyl-cellulose (commercial name: L-HPC ®, grade: LH-11, Shin-Etsu Chemical Co., Ltd.) | 5 (parts by weight) |
| Hydroxypropylcellulose (commercial name: NISSO ® HPC, grade: L, NIPPON SODA CO., LTD.) | 4 (parts by weight) wherein "2" was added as a powder, the other "2" was added as a binding solution. |
| Magnesium stearate (Taihei Chemical Industrial Co., Ltd.) | 0.5 (parts by weight) |

To prepare a powder for the first layer, the solid dispersion fine particle, polyethylene oxide, hydroxypropylcellulose, dibutylhydroxytoluene, and light anhydrous silicic acid were mixed in a drum mixer, then sodium stearyl fumarate was added thereto, and further mixed. To prepare a granule for the second layer, cilostazol, microcrystalline cellulose, low substituted hydroxypropylcellulose, and hydroxypropylcellulose (to be added as a powder) were put in a mixer granulator (Kneader NSK-350SR, OKADA SEIKO CO., LTD.), and the mixture was kneaded/granulated with 10% aqueous hydroxypropylcellulose as a binding solution, dried in FLO-COATER® (FLO-5, Freund Corporation), and size-regulated with Power Mill (P-3S type, Dalton Co., Ltd.), and then magnesium stearate was added thereto, and further mixed.

The tableting was carried out with a bi-layer tableting machine (PICCOLA BI-LAYER, RIVA) equipped with caplet-shaped (13.6×6.8 mm) dies and punches. The powder for the first layer was put on the dies and weakly compressed. Subsequently, the granule for the second layer was put around the compressed product on the same dies and compressed at a tableting pressure of about 2000 kg to prepare a bi-layer tablet containing 100 mg of cilostazol.

| Formulation Example 8 | |
|---|---|
| Solid dispersion fine particle (<500 μm) of Example 3 | 225 (parts by weight) |
| Polyethylene oxide (Polyox WSR-303, Dow Chemical) | 135 (parts by weight) |
| Hydroxypropylcellulose (commercial name: NISSO ® HPC, grade: SSL, NIPPON SODA, CO. LTD.) | 20 (parts by weight) |
| Light anhydrous silicic acid (adsolider 101, Freund Corporation) | 3 (parts by weight) |
| Dibutylhydroxytoluene (Merck Ltd.) | 0.5 (parts by weight) |
| Sodium stearyl fumarate (Rettenmaier Japan Co., Ltd.) | 1.5 (parts by weight) |

According to the above formula, the solid dispersion fine particle, polyethylene oxide, hydroxypropylcellulose, dibutylhydroxytoluene, and light anhydrous silicic acid were mixed in a drum mixer, and then sodium stearyl fumarate was added thereto and further mixed. The mixed powder was compressed with a rotary tablet press machine (Clean Press, Kikusui Seisakusho Ltd.) equipped with caplet-shaped (13.6×6.8 mm) dies and punches at a tableting pressure of 1800 kg to prepare a caplet containing 100 mg of cilostazol.

Test 5: Administration of Solid Dispersion Comprising Cilostazol to Minipigs (Evaluation of the Effect In Vivo)

To minipigs (about 9 months old, body weight 15-24 kg, NIBS, Nisseiken Co., Ltd.) which were fed 1 hour before, a gelatin capsule containing each of the solid dispersions prepared in Examples 2 and 3, and Comparative Example 3 was administered via a gavage, in which each capsule contained 200 mg of cilostazol, i.e., 400 mg of the solid dispersion for Example 2 and 600 mg of the solid dispersion for Example 3 and Comparative Example 3. Shortly after the administration, 50 mL of injectable water was administered via a stomach tube to the minipigs.

The control sample was prepared by the same administration with a cilostazol tablet (Product name: Pletaal® tablet) 100 mg.

The blood for the test was collected from a catheter inserted into the large sinus cavity. The blood collection was done at the time, before the administration; and 0.5, 1, 2, 3, 4, 6, 8, 12, 16 and 24 hours after the administration, provided that the sampling of 16 hours after the administration was skipped in the Pletaal® tablet test. The amount of blood sampling was about 1.5 mL (n=4). The collected blood was centrifuged at 3000 rpm for 15 minutes to give plasma thereof. The concentration of cilostazol in the plasma was measured with LC-MS. Based on the profile of the plasma concentration, maximum plasma concentration ($C_{max}$) and area under the plasma concentration curve (AUC), maximum plasma drug concentration time ($T_{max}$) r and mean residence time ($MRT_{last}$) were calculated.

Figure 7:
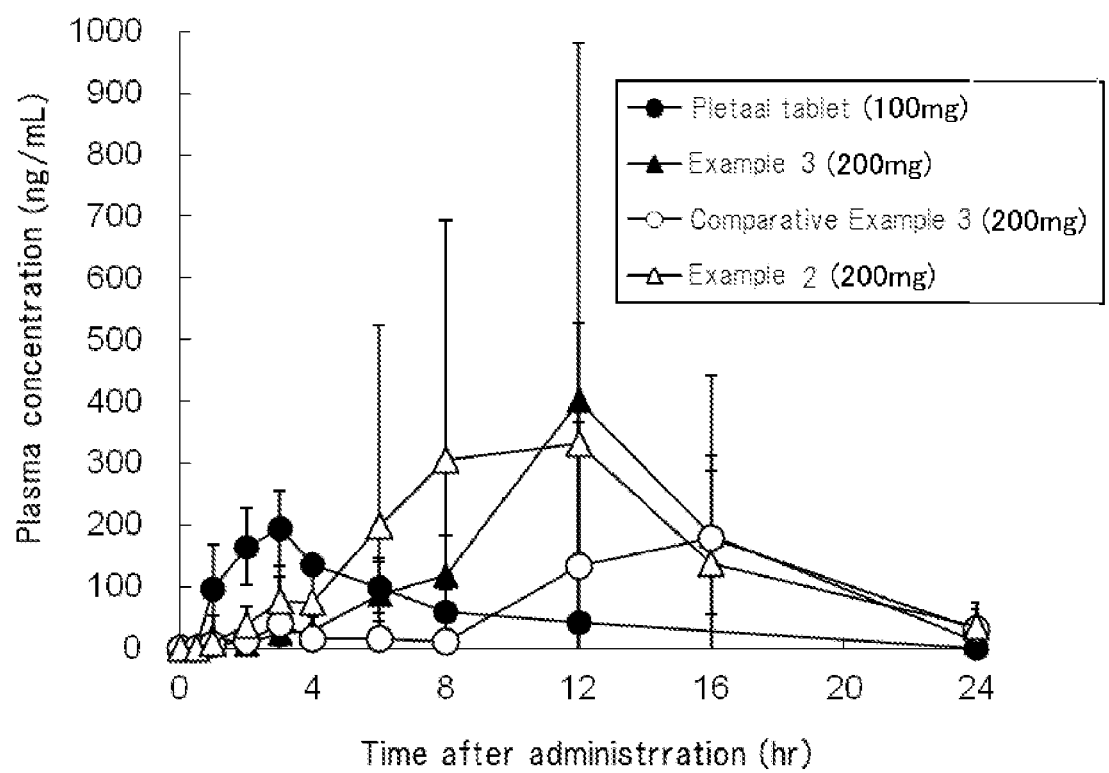
FIG. 7 represents a graph showing the profile in plasma concentration of cilostazol when each solid dispersion of Examples 2 and 3, and Comparative Example 3, and Pletaal® tablet were administered to minipigs.

The results of Test 5 are shown in Table 3 and FIG. 7.

The solid dispersions containing cilostazol of Examples 2 and 3, in which methacrylic acid copolymer S was used, exhibited higher improvement effect of the absorption in $C_{max}$ and AUC, compared with Pletaal® tablet. In addition, both of $T_{max}$ and $MRT_{last}$ of Examples 2 and 3 were markedly increased compared with Pletaal® tablet, which indicated improvement effect of the absorption in lower section of the small intestine and in the large intestine.

According to the above results, it has become clear that the solid dispersion which retains cilostazol in an amorphous state with methacrylic acid copolymer is improved on the absorption in lower section of the small intestine and in the large intestine, with the improvement of the solubility of cilostazol.

TABLE 3

| | Pletaal tablet | Example 2 | Example 3 | Comparative Example 3 |
|---|---|---|---|---|
| $C_{max}$ (ng/mL) | 196.5 | 447.3 | 490.6 | 303.7 |
| $AUC_{all}$ (ng · hr/mL) | 1349.0 | 3848.9 | 3447.9 | 1870.7 |
| $T_{max}$ (hr) | 2.8 | 14.0 | 14.0 | 17.0 |
| $MRT_{last}$ (hr) | 5.0 | 11.0 | 12.3 | 16.1 |

Test 6: Administration of Solid Dispersion Formulation Comprising Cilostazol to Dogs (Evaluation of the Effect in Vivo)

To male beagle dogs (about 30 months old, body weight 8.0-12.0 kg, Nosan Beagle, NALK CORPORATION), the hydrogel bi-layer tablet prepared in Formulation Example 6 was administered via a gavage. Shortly after the administration, 40 mL of 0.1 N aqueous hydrochloric acid was administered via a gavage. 30 minutes before the administration, about 50 g of CD5 (Oriental Yeast Co., ltd.) was given to the dogs, then the dogs were fasted until the last blood collection. As the control sample, Pletaal® tablet 100 mg was used.

The blood collection was done at the time, before the administration; and 0.5, 1, 2, 3, 4, 6, 8, 10, 12 and 24 hours after the administration, provided that the samplings of 12 and 24 hours after the administration were skipped in the Pletaal® tablet test. The amount of blood sampling was about 1 mL (n=6). The collected blood was centrifuged at 3000 rpm for 10 minutes to give serum thereof. The concentration of cilostazol in the serum was measured with LC-MS.

Based on the profile of the serum concentration, maximum serum concentration ($C_{max}$) and area under the serum concentration curve (AUC), maximum serum drug concentration time ($T_{max}$), and mean residence time ($MRT_{last}$) were calculated.

Figure 8:
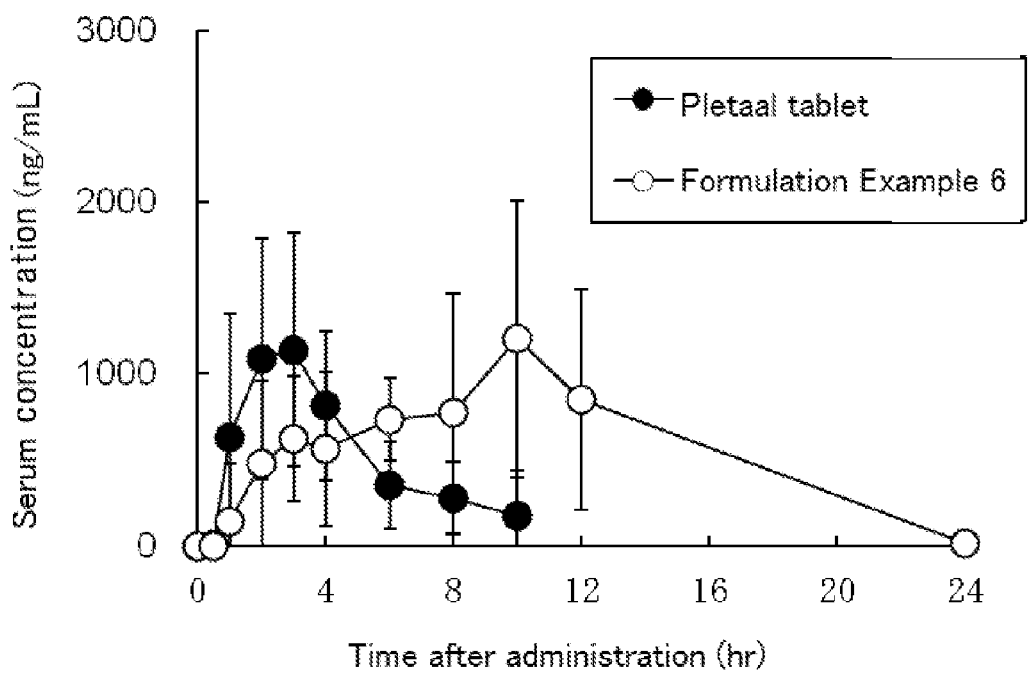
FIG. 8 represents a graph showing the profile in serum concentration of cilostazol when the tablet of Formulation Example 6 and Pletaal® tablet were administered to dogs.

The results of Test 6 are shown in Table 4 and FIG. 8.

TABLE 4

| | Pletaal tablet | Formulation Example 6 |
|---|---|---|
| $C_{max}$ (ng/mL) | 1561.4 | 1782.0 |
| $AUC_t$ (ng · hr/mL) | 5364.6 | 13544.3 |

TABLE 4-continued

|  | Pletaal tablet | Formulation Example 6 |
|---|---|---|
| $T_{max}$ (hr) | 2.83 | 9.0 |
| $MRT_{last}$ (hr) | 3.93 | 8.63 |

Test 7: Administration of Solid Dispersion Formulation Comprising Cilostazol to Dogs (Diet Effect)

To male beagle dogs (about 30 months old, body weight 8.0-12.0 kg, Nosan Beagle, NALK CORPORATION), the solid dispersion was administered via a gavage, and then the diet effect was evaluated. To the solid dispersion prepared in Example 3 (250 to 500 μm) which contains 100 mg of cilostazol, the same weight of lactose was added to increase the total weight twice. A capsule for dog was filled with the mixture and administered to the dogs. Shortly after the administration, 40 mL of 0.1 N aqueous hydrochloric acid was administered via a gavage.

For the fasting group, the dogs had been fasted from hours before the administration to the last blood collection.

For the feeding group, the dogs were given about 50 g of CD5 (Oriental Yeast Co., ltd.) 30 minutes before the administration, then the dogs had been fasted until the last blood collection.

The blood collection was done at the time, before the administration; and 0.5, 1, 2, 3, 4, 6, 8, 10, 12 and 24 hours after the administration. The amount of blood sampling was about 1 mL (n=6). The collected blood was centrifuged at 3000 rpm for 10 minutes to give serum thereof. The concentration of cilostazol in the serum was measured with LC-MS.

Based on the profile of the serum concentration, maximum serum concentration ($C_{max}$) and area under the serum concentration curve (AUC), maximum plasma drug concentration time ($T_{max}$) r and mean residence time ($MRT_{last}$) were calculated.

The results of Test 7 are shown in Table 5.

TABLE 5

|  | Fasting | Feeding |
|---|---|---|
| $C_{max}$ (ng/mL) | 1930.3 | 1466.0 |
| $AUC_t$ (ng · hr/mL) | 4779.3 | 6300.3 |
| $T_{max}$ (hr) | 3.5 | 6.3 |
| $MRT_{last}$ (hr) | 4.0 | 6.3 |

Test 8

The dissolution character of cilostazol from the tablets prepared in Formulation Examples 6, 7 and 8, and Pletaal tablet 100 mg was evaluated.

The dissolution test was carried out according to the Japanese Pharmacopoeia, Dissolution Test, Apparatus 2 (Paddle Method) wherein the test solvent was pH 6.8 phosphate buffer containing 0.3% cetyltrimethylammonium bromide. In the test, a sinker was used and the rotary speed of the paddle was 150 rpm. The solutions taken in every sampling time were analyzed with a spectrophotometer (UV 1200, SHIMADZU CORPORATION) to measure the concentration of cilostazol in each sampling solution.

Figure 9:
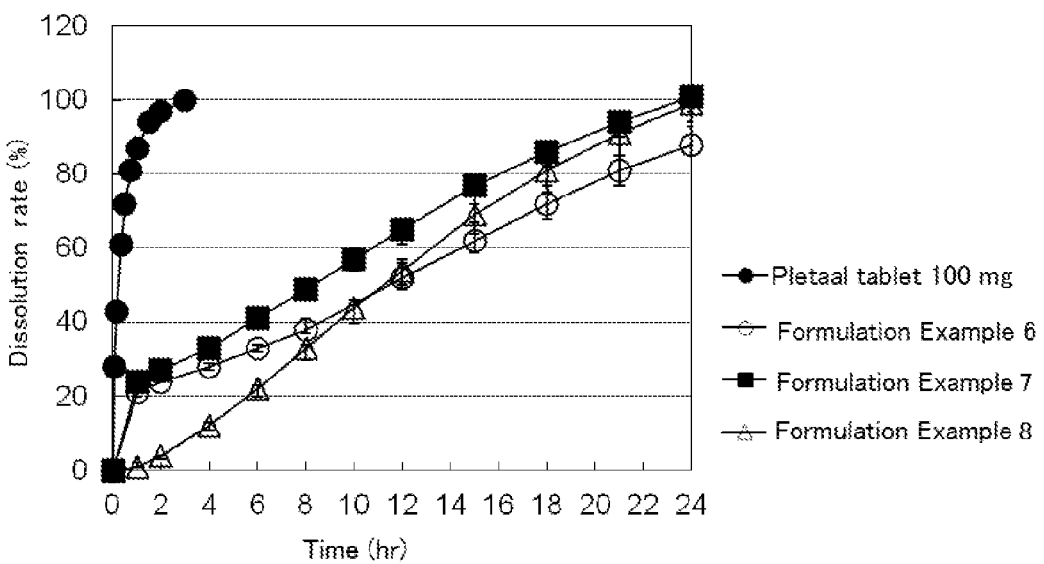
FIG. 9 represents a result in the dissolution test with the tablet of Formulation Examples 6, 7 and 8, and Pletaal® tablet in a phosphate buffer (pH 6.8) containing cetyltrimethylammonium bromide.

The result was shown in FIG. 9.

The result showed that the tablets of Formulation Examples 6, 7 and 8 have a dissolution profile of suspended release property, compared with that of Pletaal tablet 100 mg.

The invention claimed is:

1. A solid dispersion comprising (i) cilostazol and (ii) methacrylic acid copolymer S and/or methacrylic acid copolymer L wherein the ratio of (i) cilostazol and (ii) methacrylic acid copolymer S and/or methacrylic acid copolymer L is 1:1 to 1:3 by weight, which is prepared by hot-melt or hot-melt extrusion.

2. The solid dispersion of claim 1 wherein cilostazol is dispersed in an amorphous state in the methacrylic acid copolymer.

3. The solid dispersion of claim 1 which is prepared by hot-melt extrusion.

4. The solid dispersion of claim 1 wherein (ii) methacrylic acid copolymer S and/or methacrylic acid copolymer L is methacrylic acid copolymer S.

5. The solid dispersion of claim 1 wherein (ii) methacrylic acid copolymer S and/or methacrylic acid copolymer L is methacrylic acid copolymer L.

6. A pharmaceutical composition comprising the solid dispersion of claim 1.

7. The pharmaceutical composition of claim 6 further comprising polyethylene oxide.

8. A bi-layer tablet comprising the pharmaceutical composition of claim 7 as a first layer and a pharmaceutical composition comprising milled cilostazol as a second layer.

9. An oral formulation comprising the pharmaceutical composition of claim 6.

10. A process of preparing a solid dispersion which comprises
hot-melting or hot-melt extruding (i) cilostazol and (ii) methacrylic acid copolymer S and/or methacrylic acid copolymer L, wherein the ratio of (i) cilostazol and (ii) methacrylic acid copolymer S and/or methacrylic acid copolymer L is 1:1 to 1:3 by weight, and then
cooling and milling the extruded product.

* * * * *